United States Patent
Maeda

(10) Patent No.: US 9,523,927 B2
(45) Date of Patent: Dec. 20, 2016

(54) EXPOSURE APPARATUS WITH DETECTION APPARATUS FOR DETECTION OF UPPER AND LOWER SURFACE MARKS, AND DEVICE MANUFACTURING METHOD

(71) Applicant: CANON KABUSHIKI KAISHA, Tokyo (JP)

(72) Inventor: Hironori Maeda, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 400 days.

(21) Appl. No.: 13/762,476

(22) Filed: Feb. 8, 2013

(65) Prior Publication Data

US 2013/0230798 A1    Sep. 5, 2013

(30) Foreign Application Priority Data

Mar. 5, 2012 (JP) ................. 2012-048611

(51) Int. Cl.
| | |
|---|---|
| G03F 9/00 | (2006.01) |
| G01B 11/14 | (2006.01) |
| G03F 7/20 | (2006.01) |
| G01B 11/00 | (2006.01) |
| G01B 11/06 | (2006.01) |
| G01N 21/41 | (2006.01) |
| G01S 17/88 | (2006.01) |

(52) U.S. Cl.
CPC ........... *G03F 9/7084* (2013.01); *G01B 11/002* (2013.01); *G01B 11/0608* (2013.01); *G01B 11/14* (2013.01); *G01N 21/41* (2013.01); *G03F 7/70641* (2013.01); *G03F 9/7026* (2013.01); *G03F 9/7057* (2013.01); *G01S 17/88* (2013.01)

(58) Field of Classification Search
CPC ............................ G03F 9/7026; G03F 9/7084
See application file for complete search history.

(56) References Cited

U.S. PATENT DOCUMENTS

| | | | |
|---|---|---|---|
| 5,114,223 | A | 5/1992 | Torigoe et al. |
| 6,553,137 | B1 | 4/2003 | Tomimatu |
| 6,936,385 | B2 | 8/2005 | Lof et al. |
| 2008/0239271 | A1 | 10/2008 | Maeda |

(Continued)

FOREIGN PATENT DOCUMENTS

| | | |
|---|---|---|
| CN | 1442757 A | 9/2003 |
| CN | 102253603 A | 11/2011 |

(Continued)

OTHER PUBLICATIONS

Office Action issued in counterpart Chinese Patent Application No. 201310062460.2, dated Oct. 11, 2014. English translation provided.

(Continued)

*Primary Examiner* — Michelle M Iacoletti
(74) *Attorney, Agent, or Firm* — Rossi, Kimms & McDowell LLP

(57) ABSTRACT

A detection apparatus, which detects a mark formed on a lower surface of a target object, includes: a first detector which illuminates the mark from an upper surface side of the target object to detect an image of the illuminated mark; a second detector which detects an upper surface position of the target object; and a processor which obtains information indicating a focus position to focus on the mark in the first detector, based on the upper surface position detected by the second detector.

8 Claims, 15 Drawing Sheets

(56) References Cited

U.S. PATENT DOCUMENTS

| | | |
|---|---|---|
| 2009/0153825 A1 | 6/2009 | Edart et al. |
| 2011/0033790 A1 | 2/2011 | Mishima |
| 2012/0307226 A1 | 12/2012 | Maeda |

FOREIGN PATENT DOCUMENTS

| | | | |
|---|---|---|---|
| JP | 51107825 | A | 9/1976 |
| JP | 6165433 | A | 4/1986 |
| JP | 61219045 | A | 9/1986 |
| JP | 62-16526 | A | 1/1987 |
| JP | 2000294499 | A | 10/2000 |
| JP | 2002-280299 | A | 9/2002 |
| JP | 2005005444 | A | 1/2005 |
| JP | 2006242722 | A | 9/2006 |
| JP | 2007242707 | A | 9/2007 |
| JP | 2008096605 | A | 4/2008 |
| JP | 2009147317 | A | 7/2009 |

OTHER PUBLICATIONS

Korean Office Action issued in Korean counterpart application No. KR10-2013-0018971, dated Aug. 13, 2015.

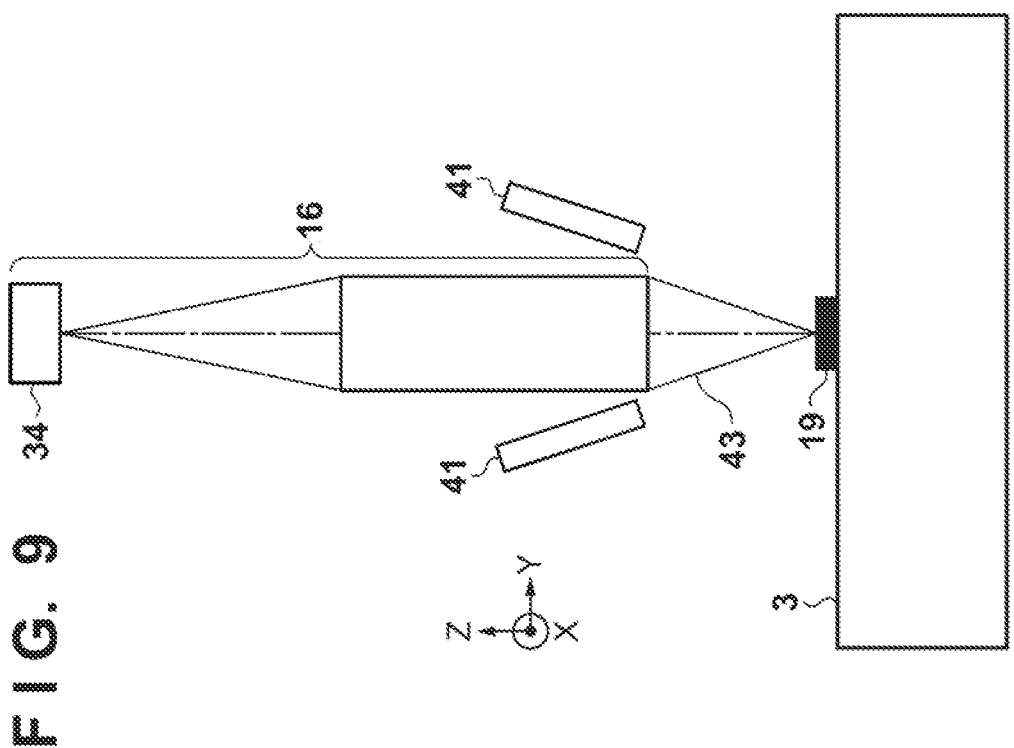
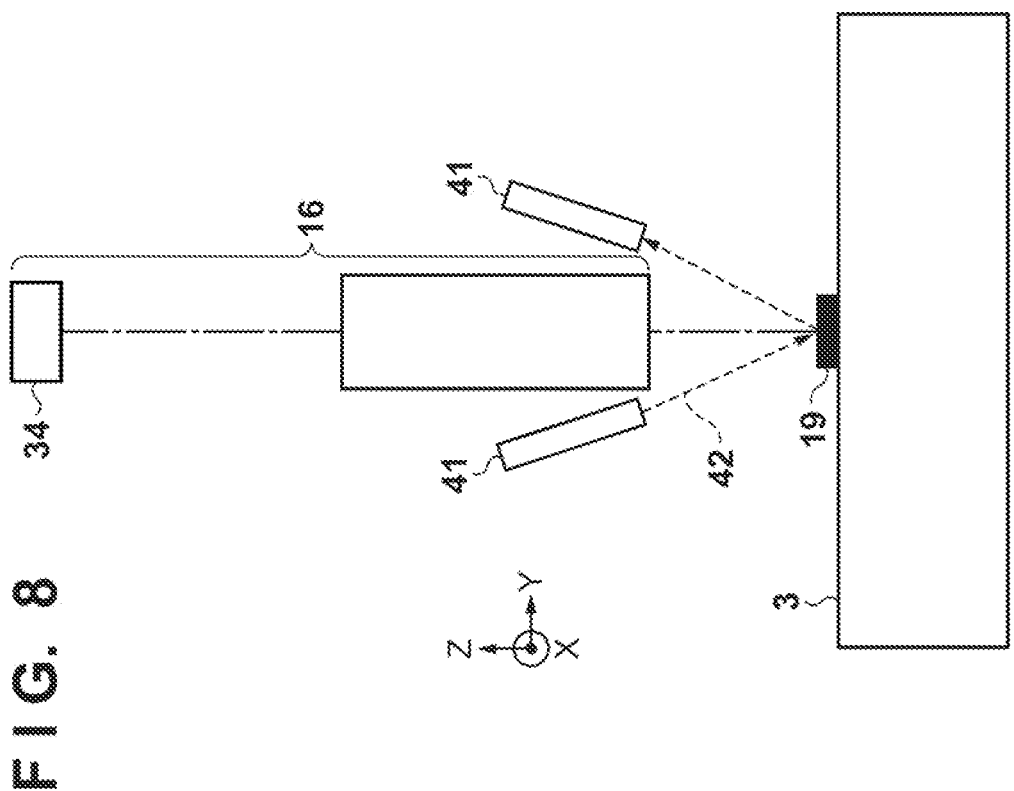

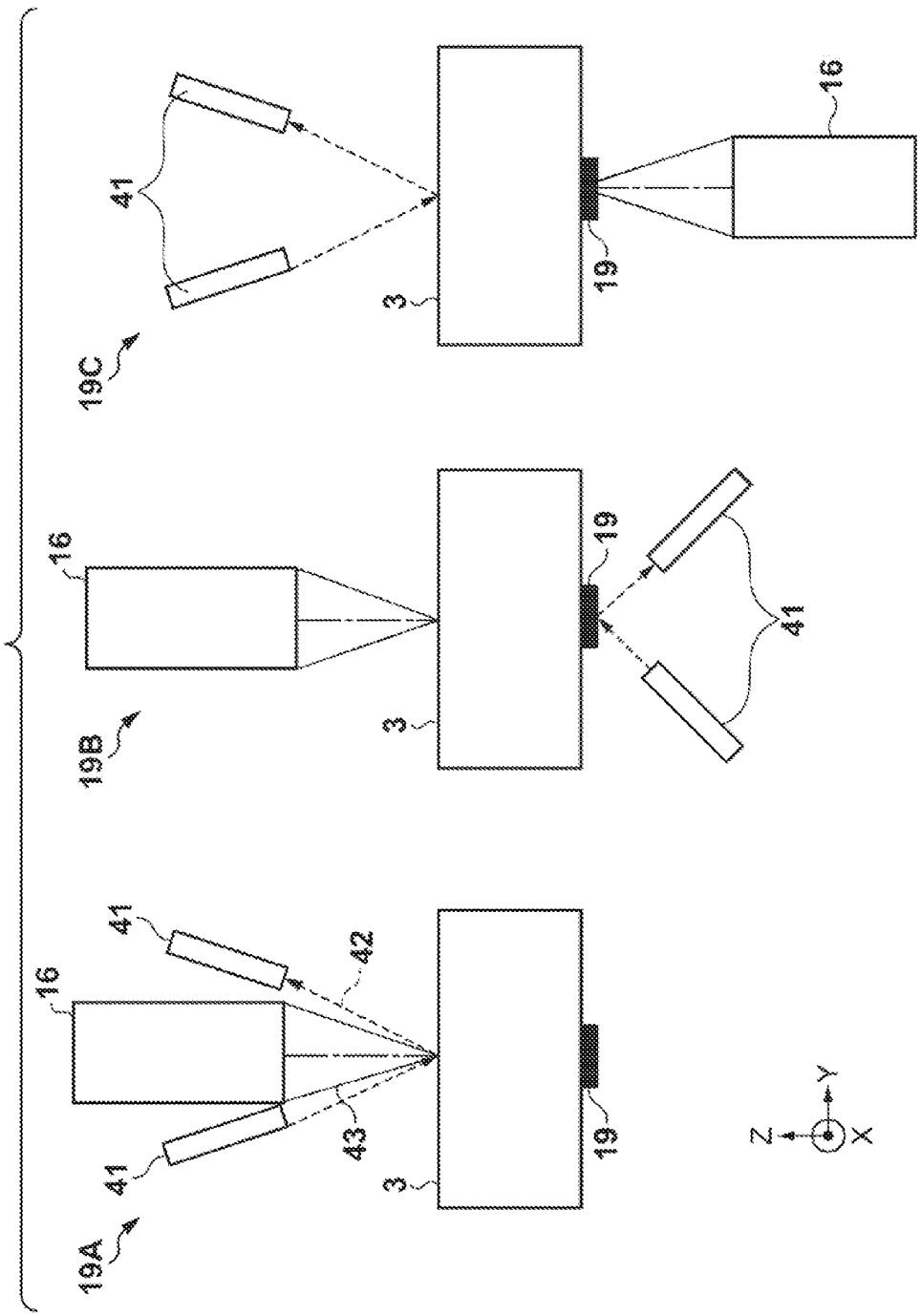

EXPOSURE APPARATUS WITH DETECTION APPARATUS FOR DETECTION OF UPPER AND LOWER SURFACE MARKS, AND DEVICE MANUFACTURING METHOD

BACKGROUND OF THE INVENTION

Field of the Invention

The present invention relates to a detection apparatus which detects a mark, formed on the lower surface of a target object, from the upper surface side of the target object, an exposure apparatus, and a method of manufacturing a device.

Description of the Related Art

To manufacture a device (for example, a semiconductor device, a liquid crystal display device, or a thin film magnetic head) using the photolithography technique, a projection exposure apparatus which projects and transfers a pattern drawn on a reticle onto, for example, a wafer by a projection optical system has been conventionally employed. At this time, an alignment detection system built into the projection exposure apparatus is used to align an image of the pattern of the reticle, which is projected via the projection optical system, with the pattern already formed on the wafer, and exposure is performed.

With miniaturization and an increase in packing density of integrated circuits, a projection exposure apparatus is required to project and transfer the pattern of a reticle onto a wafer by exposure at a higher resolution. The minimum line width (resolution) that the projection exposure apparatus can transfer is proportional to the wavelength of light used for exposure, and is inversely proportional to the numerical aperture (NA) of a projection optical system. This means that the shorter the wavelength, the higher the resolution. Hence, the recent light sources have shifted from the g-line (wavelength: about 436 nm) and i-line (wavelength: about 365 nm) of ultra-high pressure mercury lamps to a KrF excimer laser (wavelength: about 248 nm) and an ArF excimer laser (wavelength: about 193 nm). Also, the practical application of an $F_2$ laser (wavelength: about 157 nm) as a light source is in progress, so the adoption of EUV (Extreme Ultra Violet) light having wavelengths of several to one hundred nanometers is expected in the future.

The exposure apparatus has come to be used to manufacture special devices including not only the conventional IC chips such as memory and logic chips but also stacked devices, which use a through-hole via process, such as a MEMS and a CMOS image sensor (CIS). Devices such as a MEMS and a CIS are different from IC chips in several respects. In devices such as a MEMS and a CIS, demands for the line width resolution and overlay accuracy of IC chips are easy, while a large depth of focus is necessary. Also, as special processes for manufacturing devices such as a MEMS and a CIS, a process of setting an alignment target on the lower surface of an Si wafer, and exposing the upper surface of the wafer to light upon alignment with this lower surface is available. As a typical practical example, the thickness of an Si wafer is reduced, and a through-hole via is formed from the upper surface side and electrically connected to the circuit on the lower surface. A technique of detecting an alignment mark formed on the lower surface (lower surface alignment) in this way has become important these days.

Japanese Patent Laid-Open No. 2002-280299 proposes a method of using an alignment detection system set on the lower surface side (wafer chuck side) to form, on the upper surface, an image of an alignment mark formed on the lower surface, and detect the position of the alignment mark on the upper surface. However, in a method of setting an alignment detection system on the lower surface side in this way, a hole is formed at a specific position for the wafer chuck, so only the alignment mark at this position can be measured. Therefore, in the method disclosed in Japanese Patent Laid-Open No. 2002-280299, it is impossible to observe an alignment mark positioned at an arbitrary position on the lower surface of the wafer.

An Si substrate is transparent to infrared light (wavelength: 1,000 nm or more). Hence, a method of observing a mark on the lower surface from the upper surface side using a position detection system that uses infrared light as a light source has also been proposed. In a normal alignment sequence, first, to measure a best focus position of an alignment mark, an image of the alignment mark is obtained while a wafer stage is driven in the optical axis direction of a position detection system, and a position with a maximum contrast is calculated. This measurement method will be referred to as image autofocus measurement hereinafter. High-accuracy position detection can be performed by alignment at a focus position calculated by image autofocus measurement.

In image autofocus measurement, an image of an alignment mark is obtained by driving a wafer stage from the default focus position of a position detection system in the Z-direction. The default focus position of the position detection system is aligned with a reference plate positioned on a stage in an exposure apparatus. That is, in the conventional image autofocus measurement, a measurement start point is determined with reference to the level of the reference plate. However, the level of the upper surface of the wafer is often different from that of the reference plate, depending on the degree of suction of a wafer in mounting the wafer on the wafer stage. In this case, it is impossible to start image autofocus measurement for an alignment mark on the upper surface of an Si substrate, precisely from the upper surface of the Si substrate. However, when image autofocus measurement starts from the level of the reference plate, it is possible to quickly, easily detect the mark on the upper surface of the Si substrate.

However, when an alignment mark is present on the lower surface of the Si substrate, it is normally problematic in that the position detection system focuses on the reference plate. When the wafer stage is driven from the reference plate at the default focus position of the position detection system, a large search range is necessary to detect the alignment mark on the lower surface of the Si substrate. When a large search range is set to measure the alignment mark on the lower surface of the Si substrate, the measurement operation takes a considerable time, thus lowering the throughput. Also, the calculation error of a best focus position of the alignment mark also increases as the measurement pitch of image autofocus measurement increases, thus making it impossible to perform high-accuracy alignment.

SUMMARY OF THE INVENTION

The present invention quickly, accurately detects the position of a mark formed on the lower surface of a target object.

The present invention in its first aspect provides a detection apparatus which detects a mark formed on a lower surface of a target object, the apparatus comprising: a first detector which illuminates the mark from an upper surface side of the target object to detect an image of the illuminated mark; a second detector which detects an upper surface position of the target object; and a processor which obtains information indicating a focus position to focus on the mark in the first detector, based on the upper surface position detected by the second detector.

The present invention in its second aspect provides an exposure apparatus which exposes a substrate to light, the apparatus comprising: a detection apparatus which detects at least one of a mark formed on a lower surface of a substrate as a target object, and a mark arranged on a lower surface of a resist as a target object coated on the substrate; a substrate stage which holds the substrate; and a control unit which controls the substrate stage to set a focus state of the mark to fall within an allowable range, the detection apparatus including: a first detector which illuminates the mark from an upper surface side of the target object to detect an image of the illuminated mark; a second detector which detects an upper surface position of the target object; and a processor which obtains information indicating a focus position to focus on the mark in the first detector, based on the upper surface position detected by the second detector, wherein the control unit controls the substrate stage based on the information obtained by the processor.

The present invention in its third aspect provides a method of manufacturing a device, the method comprising: exposing a substrate to light using an exposure apparatus; developing the exposed substrate; and processing the developed substrate to manufacture the device, the exposure apparatus including: a detection apparatus which detects at least one of a mark formed on a lower surface of the substrate as a target object, and a mark arranged on a lower surface of a resist as a target object coated on the substrate; a substrate stage which holds the substrate; and a control unit which controls the substrate stage to set a focus state of the mark to fall within an allowable range, the detection apparatus including: a first detector which illuminates the mark from an upper surface side of the target object to detect an image of the illuminated mark; a second detector which detects an upper surface position of the target object; and a processor which obtains information indicating a focus position to focus on the mark in the first detector, based on the upper surface position detected by the second detector, wherein the control unit controls the substrate stage based on the information obtained by the processor.

The present invention in its fourth aspect provides a detection apparatus which illuminates a mark, formed on a lower surface of a target object, from an upper surface side of the target object to detect an image of the illuminated mark, the apparatus comprising: a control unit which controls to detect the mark in a first detection mode in which the mark is detected with a first detection accuracy while changing an interval between the detection apparatus and the mark at a first pitch, and a second detection mode in which the mark is detected with a second detection accuracy higher than the first detection accuracy while changing the interval at a second pitch smaller than the first pitch; and a processor which obtains information indicating a focus position to focus on the mark in the second detection mode of the detection apparatus, based on the result of detecting the mark in the first detection mode, wherein the control unit controls the substrate stage based on the information obtained by the processor.

Further features of the present invention will become apparent from the following description of exemplary embodiments with reference to the attached drawings.

BRIEF DESCRIPTION OF THE DRAWINGS

FIG. 8 is a view showing how an alignment mark on the upper surface is measured by the AF detector;
FIG. 9 is a view showing how the alignment mark on the upper surface is measured by a wafer alignment detector;
FIG. 19 is view illustrating an example of the layout of a wafer alignment detector and an AF detector.

DESCRIPTION OF THE EMBODIMENTS

Embodiments of the present invention will be described in detail below with reference to the accompanying drawings.

First Embodiment

Figure 3:
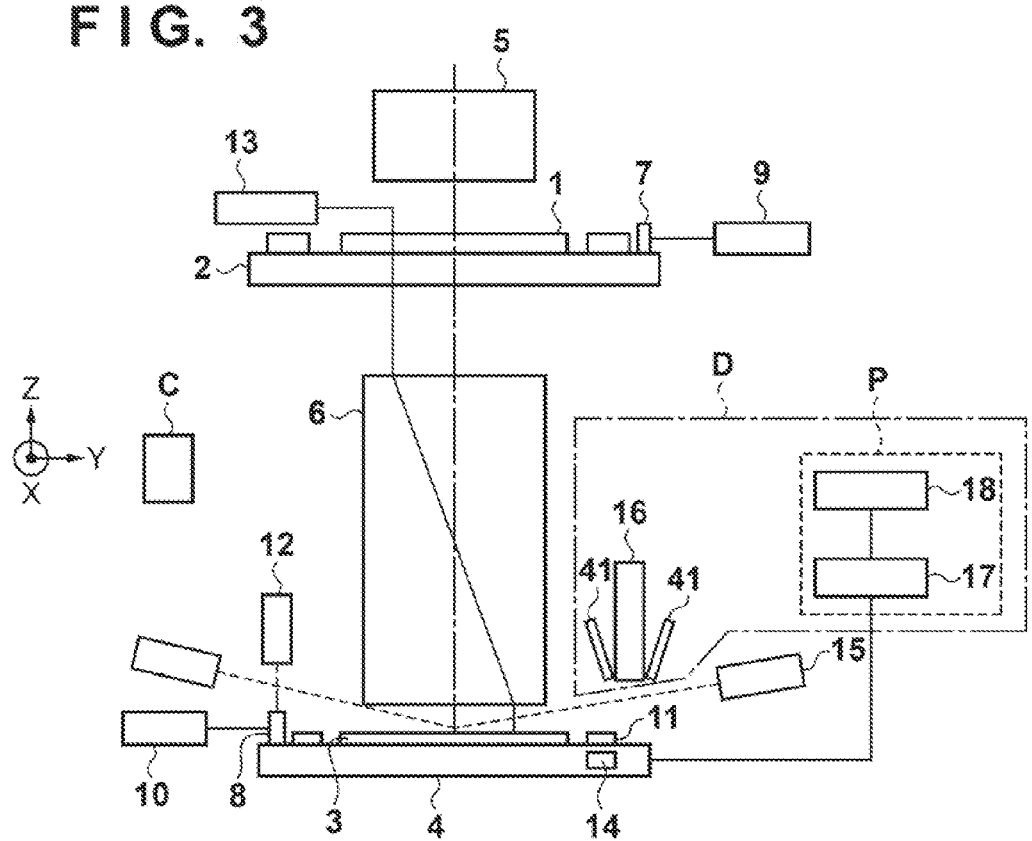
FIG. 3 is a view showing an exposure apparatus.

An exposure apparatus capable of measuring an alignment mark (mark) 19 on the lower surface of a wafer (target object) 3 at high speed and high accuracy, based on the thickness and refractive index of the target object, will be described with reference to FIG. 3. The exposure apparatus includes a detection apparatus including a wafer alignment detector (first detector) 16 shown in FIG. 1, and a focus detector (second detector) 41 which assists in detecting a best focus position of the wafer alignment detector 16 by detecting the upper surface position of the wafer 3. The focus detector (second detector) 41 will be referred to as an "AF detector" hereinafter. The exposure apparatus also includes a reticle stage 2, wafer stage (substrate stage) 4, illumination optical system 5, projection optical system 6, and control unit C. The reticle stage 2 supports a reticle (mask) 1. The wafer stage 4 supports the wafer (substrate) 3. The illumination optical system 5 illuminates the reticle 1 with exposure light. The projection optical system 6 projects a pattern image of the reticle 1 illuminated with the exposure light onto the wafer 3 supported by the wafer stage 4. The control unit C systematically controls the operation of the overall exposure apparatus.

In the first embodiment, a scanning exposure apparatus (scanning stepper) which projects and transfers a pattern formed on the reticle 1 onto the wafer 3 by exposure while moving the reticle 1 and the wafer 3 in synchronism with each other in the scanning direction is used as the exposure apparatus. The exposure apparatus may also serve as an exposure apparatus (stepper) which projects and transfers the pattern of the reticle 1 onto the wafer 3 by exposure while the reticle 1 is fixed in position. A direction which coincides with the optical axis of the projection optical system 6 is defined as the Z-direction, the direction (scanning direction) in which the reticle 1 and the wafer 3 move in synchronism with each other within a plane perpendicular to the Z-direction is defined as the Y-direction, and a direction (non-scanning direction) perpendicular to the Z- and Y-directions is defined as the X-direction. Also, rotation directions about the X-, Y-, and Z-axes are defined as the θX-, θY-, and θZ-directions, respectively.

A predetermined illumination region on the reticle 1 is illuminated with exposure light having a uniform illuminance distribution by the illumination optical system 5. As a source of exposure light emitted by the illumination optical system 5, in place of the conventionally mainstream mercury lamp, a KrF excimer laser has come to be used, and the practical application of an ArF excimer laser and $F_2$ laser that have shorter wavelengths is also in progress. Further, to manufacture, for example, a more minute semiconductor device in the future, an exposure apparatus which uses EUV (Extreme Ultra Violet) light having wavelengths of several to one hundred nanometers as exposure light is under development.

The reticle stage 2 is capable of two-dimensional movement within a plane perpendicular to the optical axis of the projection optical system 6, that is, within the X-Y plane, and minute rotation in the θZ-direction. The reticle stage 2 can be driven in at least one axial direction, but may be able to be driven in six axial directions. The reticle stage 2 is driven by a driver (not shown) such as a linear motor, and the driver is controlled by the control unit C. A mirror 7 is set on the reticle stage 2, and an X-Y laser interferometer 9 is set at a position at which it is opposed to the mirror 7. The position, in the two-dimensional direction, and the rotation angle of the reticle 1 are measured in real time by the laser interferometer 9, and the measurement result is output to the control unit C. The control unit C drives the driver of the reticle stage 2 based on the measurement result obtained by the laser interferometer 9 to position the reticle 1 supported by the reticle stage 2.

The projection optical system 6 projects and transfers the pattern of the reticle 1 onto the wafer 3 by exposure at a predetermined projection magnification β, and is formed by a plurality of optical elements. The projection optical system 6 serves as a reduction projection system having a projection magnification β of, for example, ¼ or ⅕. The wafer stage 4 includes a Z stage which holds the wafer 3 through a wafer chuck, an X-Y stage which supports the Z stage, and a base which supports the X-Y stage. The wafer stage 4 is driven by a driver (not shown) such as a linear motor. The driver of the wafer stage 4 is controlled by the control unit C.

A mirror 8 is set on the wafer stage 4. An X-Y laser interferometer 10 and a Z laser interferometer 12 are set at positions at which they are opposed to the mirror 8. The position, in the X- and Y-directions, and θZ of the wafer stage 4 are measured in real time by the laser interferometer 10, and the measurement result is output from the control unit C. Also, the position, in the Z-direction, and θX and θY of the wafer stage 4 are measured in real time by the laser interferometer 12, and the measurement result is output to the control unit C. An X-Y-Z stage is driven through the driver of the wafer stage 4 based on the measurement results obtained by the laser interferometers 10 and 12 to adjust the position of the wafer 3 in the X-, Y-, and Z-directions, and the wafer 3 supported by the wafer stage 4 is positioned.

A reticle alignment detector 13 which detects a reference mark 39 (FIG. 4) formed on a reference plate 11 on the wafer stage 4 through the projection optical system 6 and a reference mark (not shown) on the reticle 1 is set near the reticle stage 2. The reticle alignment detector 13 includes a photoelectric conversion element (for example, a CCD camera) which uses the same light source as that, which exposes the wafer 3 to light, to irradiate the reference mark 39 and the reference mark on the reticle 1 through the projection optical system 6, and detects light reflected by them. The reticle alignment detector 13 can align the relative positional relationship (X, Y, Z) between the reticle 1 and the wafer 3 by matching the positions and focuses of the reference mark on the reticle 1, and that of the reference mark 39 on the reference plate 11.

A reflective reference mark 39 may be detected by the reticle alignment detector 13, or transparent reference mark 39 can be detected using a transparent reticle alignment detector 14. The transparent reticle alignment detector 14 includes a light amount sensor which uses the illumination optical system 5 and the same light source as that, which exposes the wafer 3 to light, to irradiate the reference mark 39 and the reference mark on the reticle 1 through the projection optical system 6, and detects light transmitted through them. The positions and focuses of the reference mark on the reticle 1 and the reference mark 39 on the reference plate 11 can be matched by measuring the amount of transmitted light while the wafer stage 4 is driven in the X- (or Y-) and Z-directions. In this manner, the relative positional relationship (X, Y, Z) between the reticle 1 and the wafer 3 can be aligned using either of the reticle alignment detector 13 and the transparent reticle alignment detector 14.

Figure 4:
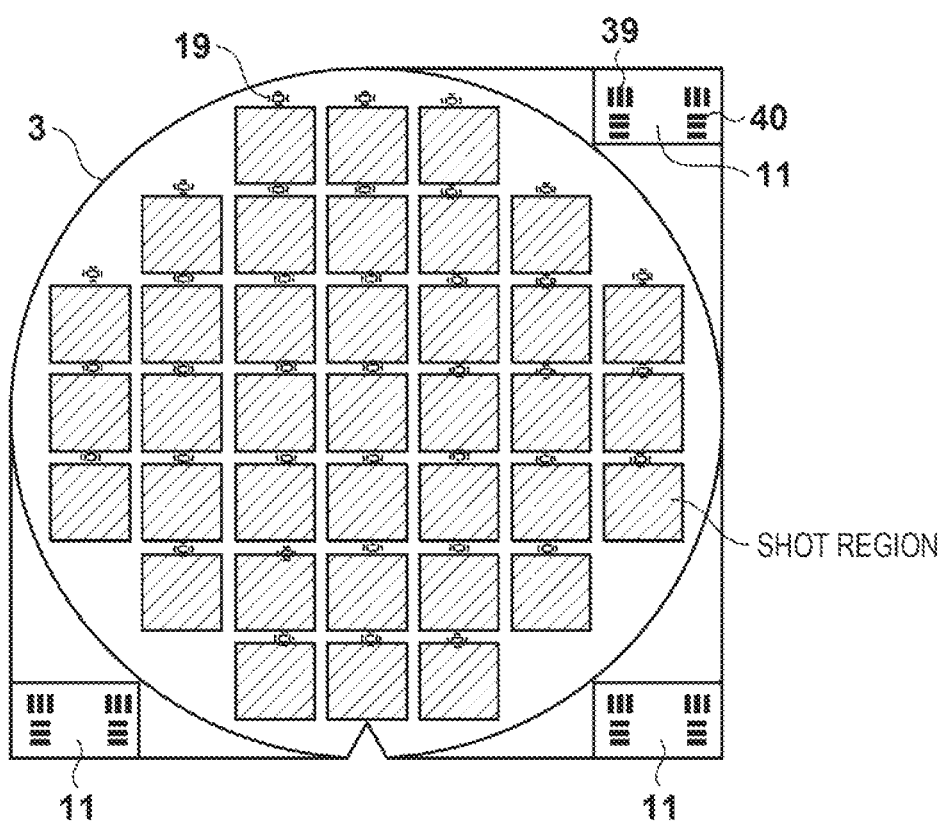
FIG. 4 is a view showing a wafer and alignment marks.

The reference plate 11 is placed at the corner of the wafer stage 4 to be nearly flush with the upper surface of the wafer 3, as shown in FIG. 4. The reference plate 11 includes a reference mark 40 to be detected by the wafer alignment detector 16, and the reference mark 39 to be detected by the reticle alignment detector 13 or transparent reticle alignment detector 14. Reference plates 11 may be positioned at a plurality of corners of the wafer stage 4. Also, the reference plate 11 may include a plurality of reference marks 39 and a plurality of reference marks 40. The positional relationship (in the X- and Y-directions) between the reference mark 39 for reticle alignment, and the reference mark 40 for wafer alignment is known. Also, the reference mark 40 for wafer alignment detection, and the reference mark 39 for reticle alignment may be a common mark.

A focus detector 15 includes a light projecting system which projects detection light onto the upper surface of the wafer 3, and a light receiving system which receives light reflected by the wafer 3, and outputs the detection result obtained by the focus detector 15 to the control unit C. The control unit C drives the Z stage based on the detection result obtained by the focus detector 15, and adjusts the position in the Z-direction (focus position), and the angle of tilt of the wafer 3 held by the Z stage to fall within allowable ranges.

The wafer alignment detector 16 includes a light projecting system which projects detection light onto the mark 19 on the wafer 3 and the reference mark 40 for wafer alignment detection on the reference plate 11, and a light receiving system which receives light reflected by them. The detection result obtained by the wafer alignment detector 16 is output to the control unit C. The control unit C can adjust the position, in the X- and Y-directions, of the wafer 3 held by the wafer stage 4 by driving the wafer stage 4 in the X- and Y-directions based on the detection result obtained by the wafer alignment detector 16. The exposure apparatus includes a focus detector (AF detector) 41 which detects the upper surface position of the wafer 3 to quickly obtain a best focus position of the wafer alignment detector 16. Like the focus detector 15, the focus detector 41 includes a light projecting system which projects detection light onto the upper surface of the wafer 3, and a light receiving system which receives light reflected by the wafer 3. The focus detector 15 is used to obtain a best focus position of the projection optical system 6, while the AF detector 41 is used to obtain a best focus position of the wafer alignment detector 16. A relative position between the AF detector 41 and the wafer alignment detector 16 is given. Both the AF detector 41 and the wafer alignment detector 16 can be fixed. Otherwise, the AF detector 41 and the wafer alignment detector 16 can be movable but the AF detector 41 and the wafer alignment detector 16 are preliminarily set in their predetermined positions.

As the wafer alignment detector 16, roughly two types of detectors are available. The wafer alignment detector 16 of the first type employs an off-axis alignment detection system (Off-axis AA or OA detection scheme) which is configured independently, without the mediacy of the projection optical system 6, and optically detects the reference mark 40 and the mark 19 on the wafer 3. The wafer alignment detector 16 of the second type employs a TTL-AA (Through The Lens Alignment) scheme which is used especially for an i-line exposure apparatus and in which the mark 19 and reference mark 40 are detected using the alignment wavelength of non-exposure light via the projection optical system 6. Although an OA detection wafer alignment detector 16 is used in this embodiment, a TTL-AA wafer alignment detector 16 may be used.

Figure 1:
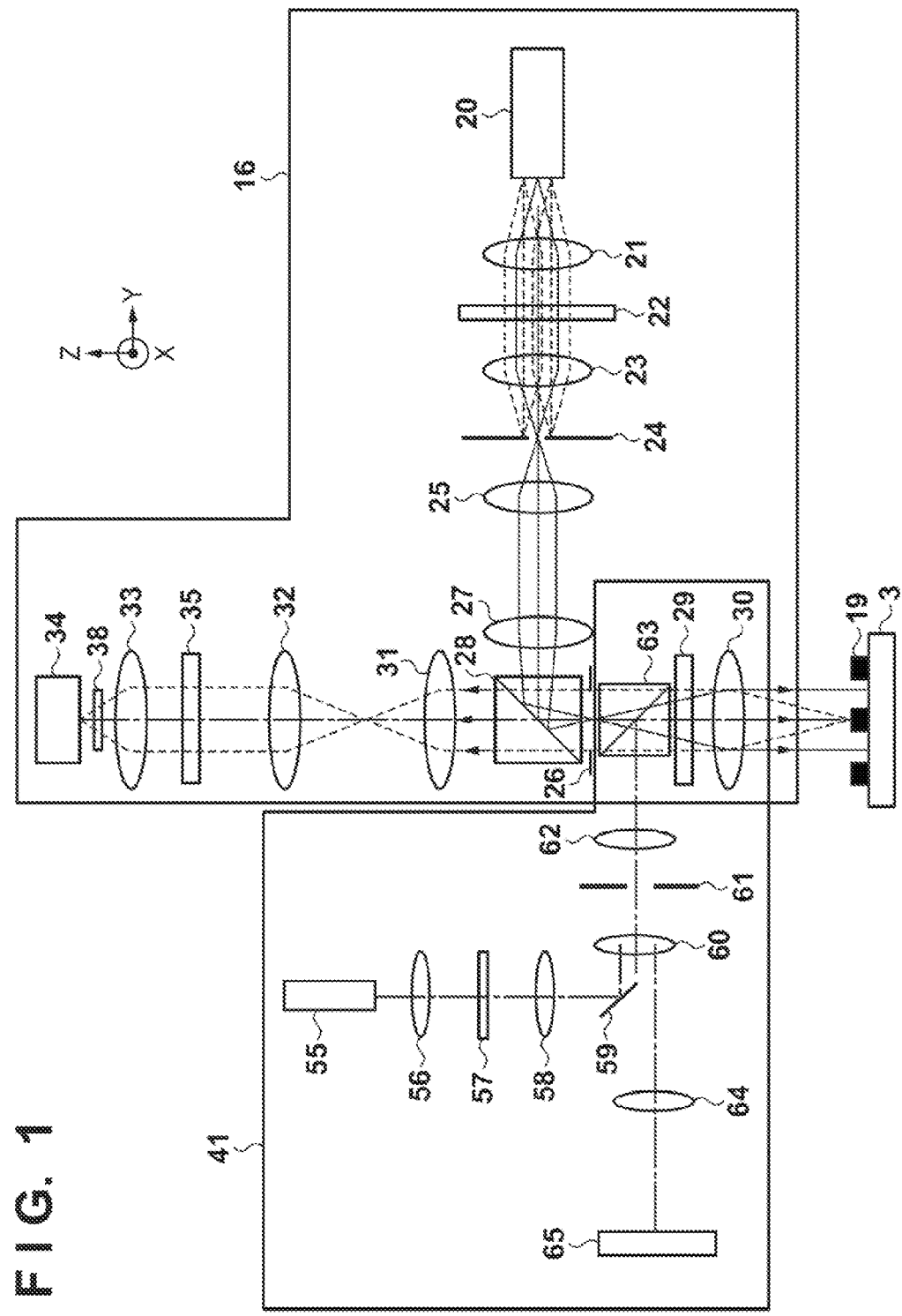
FIG. 1 is a view showing a wafer alignment detector.
Figure 2:
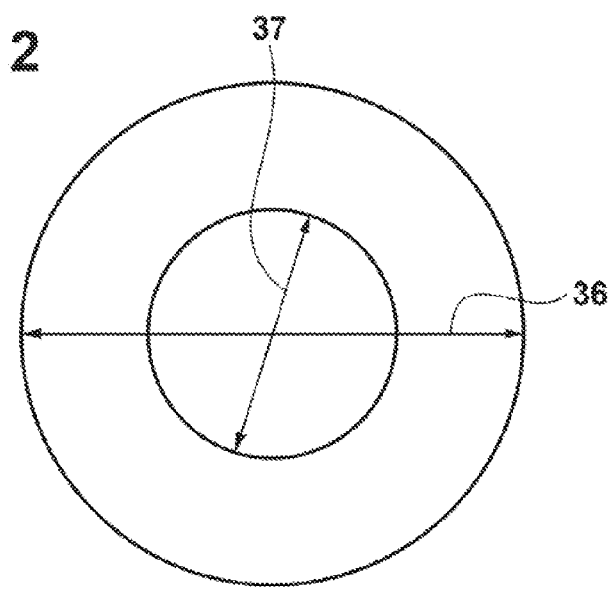
FIG. 2 is a view showing a light source and the beam diameter at a pupil position.

FIG. 1 shows details of how to observe the wafer 3 by the wafer alignment detector 16. An illumination light source 20 of the wafer alignment detector 16 emits infrared light (for example, 1,000 to 1,500 nm) and visible light (for example, 400 to 800 nm). Light emitted by the illumination light source 20 passes through a first relay optical system 21, a wavelength filter plate 22, and a second relay optical system 23, and reaches an aperture stop 24 positioned on the pupil plane (an optical Fourier transform plane for the object plane) of the wafer alignment detector 16. A beam diameter 37 in the aperture stop 24 is sufficiently smaller than a beam diameter 36 in the illumination light source 20, as shown in FIG. 2.

The wavelength filter plate 22 includes a plurality of filters in different transmission wavelength ranges, and switches between these filters in accordance with a command from the control unit C. The aperture stop 24 includes a plurality of stops having different illumination coherence factors σ, and can change the illumination coherence factor σ by switching between these stops in accordance with a command from the control unit C. Although each of the wavelength filter plate 22 and aperture stop 24 includes a plurality of filters and a plurality of stops in this embodiment, filters and stops may be added independently of the wavelength filter plate 22 and aperture stop 24. The wavelength filter plate 22 in this embodiment includes a filter which transmits visible light, and a filter which transmits infrared light, and the wavelength of light to be used in mark detection can be selected by switching between these filters. In measuring a mark formed on the lower surface of an Si substrate transparent to infrared light, a filter which transmits infrared light is used.

The light that has reached the aperture stop 24 is guided to a polarizing beam splitter 28 upon passing through a first illumination optical system 25 and a second illumination optical system 27. S-polarized light, perpendicular to the paper surface of FIG. 1, reflected by the polarizing beam splitter 28 is converted into circularly polarized light upon being transmitted through an NA stop 26, a prism 63, and a λ/4 plate 29, and illuminates the mark 19 formed on the wafer 3 upon passing through an objective lens 30 (illumination light is indicated by a solid line in FIG. 1). The NA of the NA stop 26 can be changed by changing the aperture value. The aperture value of the NA stop 26 can be changed in accordance with a command from the control unit C. Although the prism 63 will be described later with reference to FIG. 5, it has a property of transmitting alignment light.

Light beams (indicated by alternate long and short dashed lines in FIG. 1) reflected, diffracted, and scattered by the mark 19 are converted into P-polarized light parallel to the paper surface of FIG. 1 upon passing through the objective lens 30 and λ/4 plate 29 again. The P-polarized light is transmitted through the prism 63 and polarizing beam splitter 28, and passes through a relay lens 31, a first imaging optical system 32, an optical member 35 which adjusts coma, a second imaging optical system 33, and an optical member 38 which adjusts the wavelength shift difference. The P-polarized light having passed through the optical member 38 forms a detection signal of the mark 19 on a photoelectric conversion element 34 (for example, a CCD camera).

Normally, when the wafer alignment detector 16 observes the mark 19 to detect the position of the mark 19, monochromatic light or light in a narrow wavelength range generates interference fringes because of the presence of a transparent layer coated or formed on the mark 19. When this happens, the mark 19 is detected while a signal of interference fringes is added to an alignment signal, thus making it impossible to detect the mark 19 with high accuracy. Therefore, to detect the mark 19 as a signal with less interference fringes, an illumination light source having wavelengths in a wide range is generally used as the illumination light source 20 of the wafer alignment detector 16.

Figure 5:
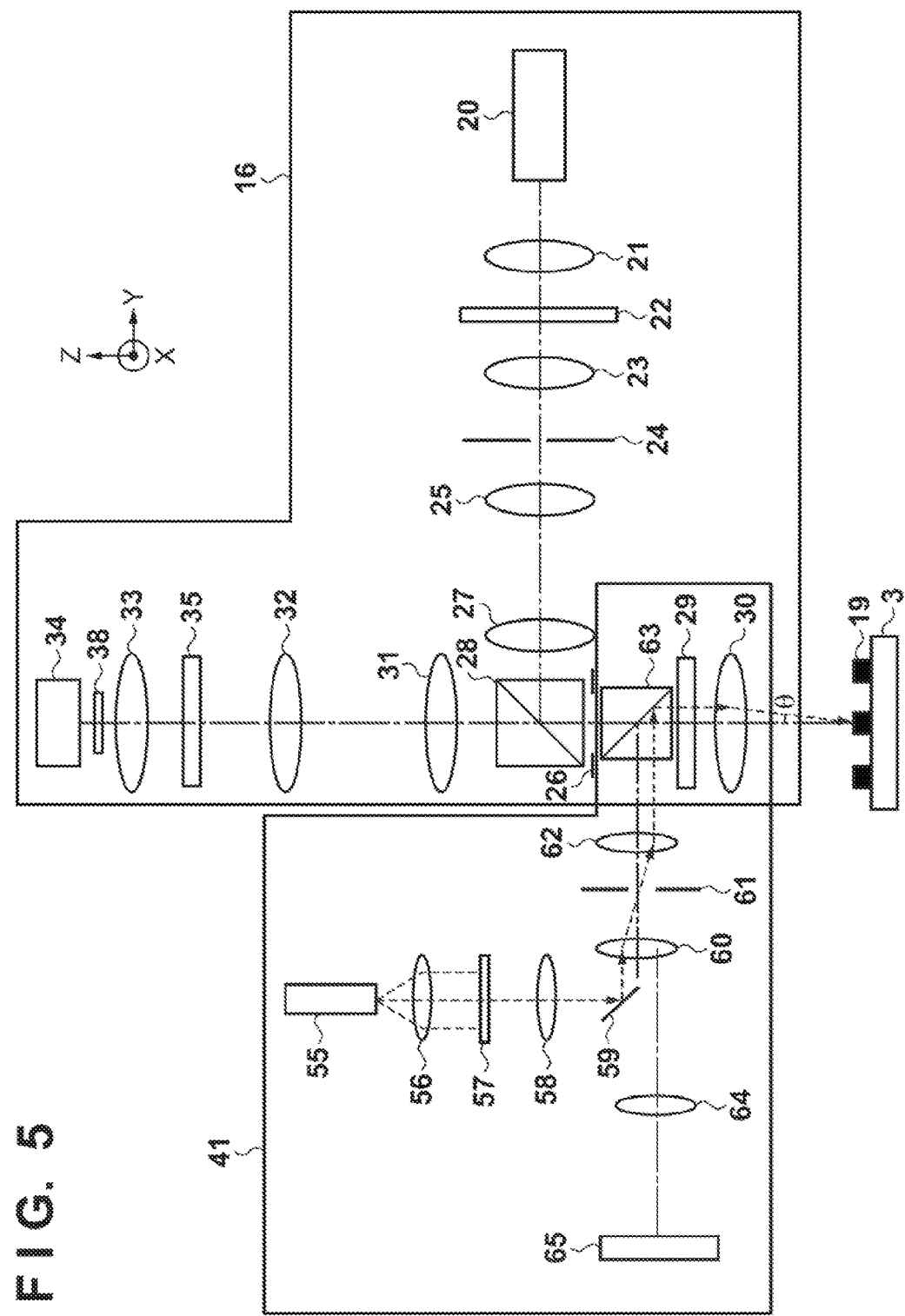
FIG. 5 is a view showing how an AF detector irradiates the wafer with AF light.
Figure 6:
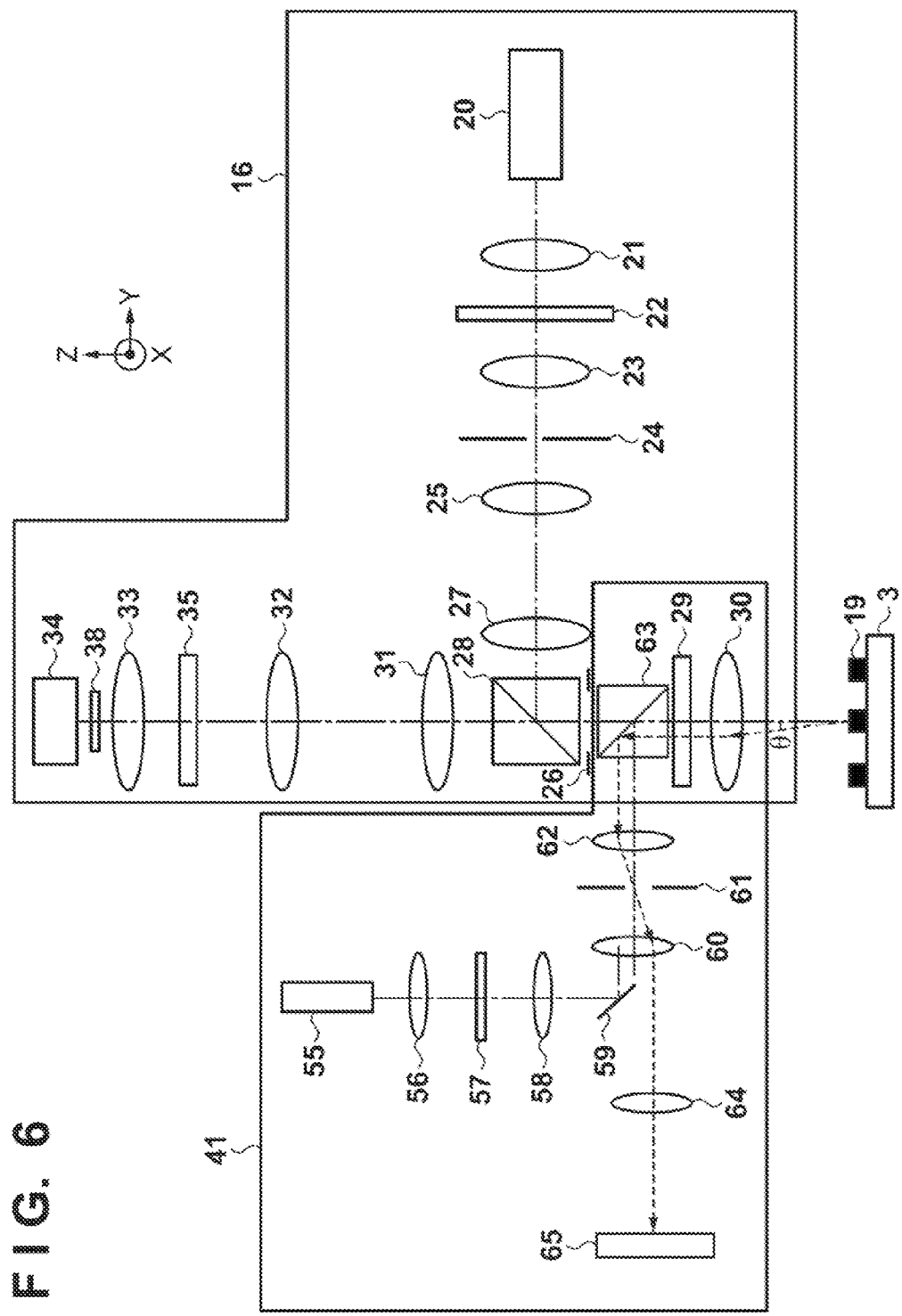
FIG. 6 is a view showing how measurement light from the wafer is received by the AF detector.

FIGS. 5 and 6 show how focus measurement is performed by the focus detector 41. FIG. 5 shows how the focus detector 41 irradiates the wafer 3 with focus measurement light (AF light). FIG. 6 shows how the irradiating AF light is reflected by the wafer 3, and received by the focus detector 41. AF light emitted by a light source 55 illuminates a pattern plate 57 through a lens 56. The light source 55 emits light in a visible wavelength range (wavelengths of 400 to 800 nm, which are not transmitted through Si). The AF light incident on the wafer 3 is not transmitted through the wafer 3. The pattern plate 57 is formed by drawing a slit pattern in a glass substrate. The AF light which illuminates the slit pattern drawn at the central portion of the pattern plate 57 reaches a lens 60 upon being reflected by a mirror 59 through a lens 58. Although only the principal ray of the AF light subsequent to the pattern plate 57 is shown in FIG. 1 for the sake of simplicity, it has a given NA in practice. The AF light reaches not the center of the lens 60 but a portion decentered from the center of the lens 60, and is refracted by the lens 60, thereby passing through a reference mirror 61, and reaching a lens 62. The light that has reached the lens 62 reaches not the center of the lens 62 but a portion decentered from the center of the lens 62. The AF light refracted by the lens 62 reaches the prism 63. The prism 63 has a property of reflecting AF light, and transmitting light used in alignment.

The AF light reflected by the prism 63 is transmitted through the λ/4 plate 29 and reaches the objective lens 30. The AF light reaches not the center of the objective lens 30 but a portion decentered from the center of the objective lens 30, and is refracted by the objective lens 30, thereby being obliquely incident on the wafer 3 at an incident angle θ, as shown in FIG. 5.

How the AF light obliquely incident on the wafer 3 is received by the focus detector 41 will be described with reference to FIG. 6. The AF light is reflected by the wafer 3 at the same angle θ as in illumination, and reaches the objective lens 30. At this time, the AF light reaches not the center of the objective lens 30 but a portion decentered from the center of the objective lens 30, and is refracted by the lens 30, thereby being transmitted through the λ/4 plate 29 and reaching the prism 63. The AF light reflected by the prism 63 reaches the lens 62. At this time, the AF light reaches not the center of the lens 62 but a portion decentered from the center of the lens 62, and is refracted by the lens 62, thereby passing through the reference mirror 61, and reaching the lens 60. At this time, the AF light reaches not the center of the lens 60 but a portion decentered from the center of the lens 60, and is refracted by the lens 60, thereby reaching the center of a lens 64, being transmitted through the lens 64, and being received by an AF detection sensor 65.

How the AF light is guided to be obliquely incident on the wafer 3 by the focus detector 41, and is received by the AF detection sensor 65 has been described with reference to FIGS. 5 and 6. As can be seen from the foregoing description, with movement of the wafer 3 in the focus direction (Z-direction), the position at which the AF light is received by the AF detection sensor 65 shifts. In this manner, the focus detector 41 can measure the upper surface position of the wafer 3.

Figure 7:
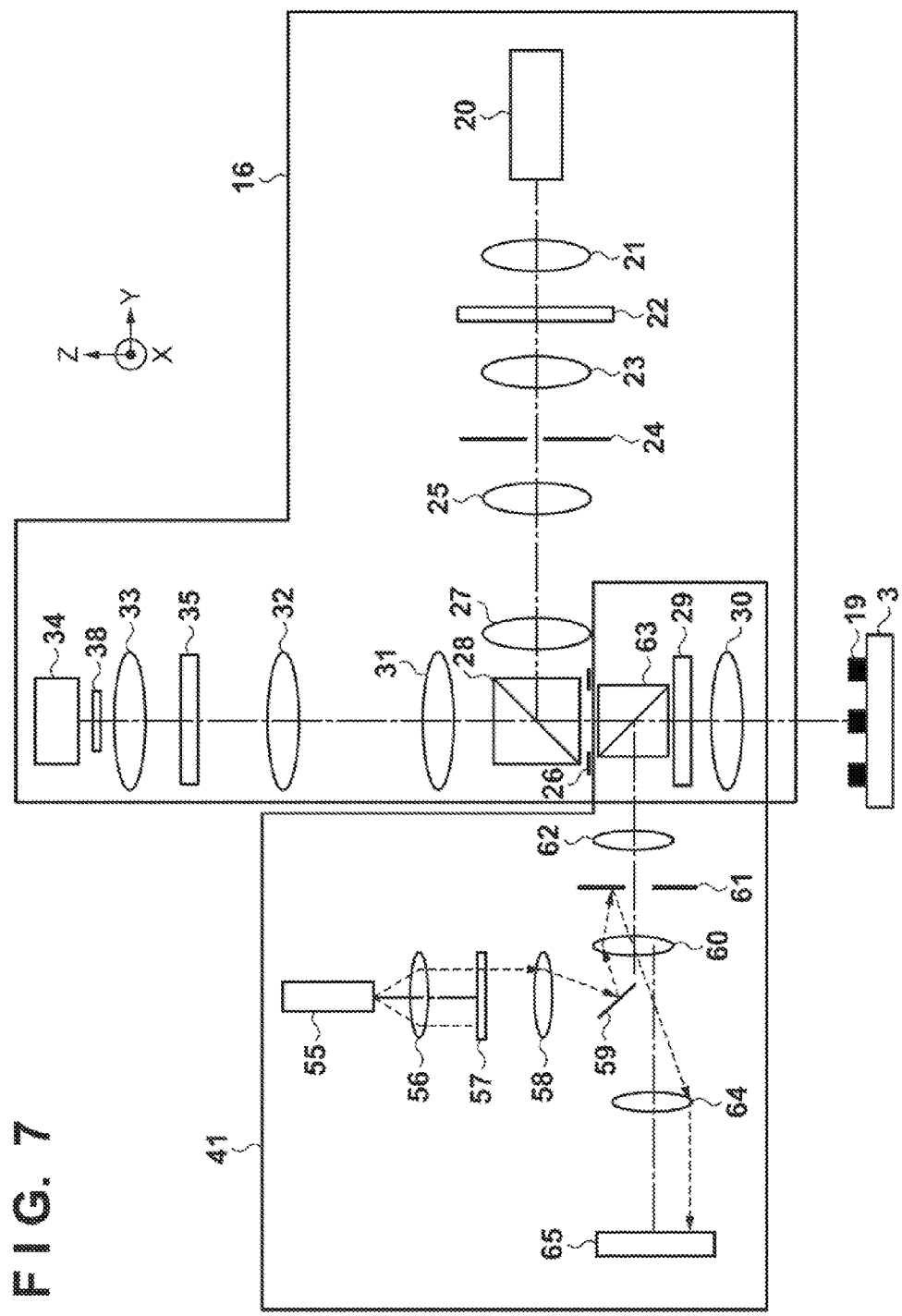
FIG. 7 is a view showing measurement by the AF detector.

FIG. 7 is a view showing how a reference within the AF detector 41 is measured. The AF light which illuminates the peripheral portion of the pattern plate 57 reaches a portion decentered from the center of the lens 58, is refracted by the lens 58, and is reflected by the mirror 59. The AF light reflected by the mirror 59 reaches a portion decentered from the center of the lens 60, is refracted by the lens 60, is reflected by the reference mirror 61, and reaches the center of the lens 60. The AF light transmitted through the center of the lens 60 reaches a portion decentered from the center of the lens 64, is refracted by the lens 64, and is received by the AF detection sensor 65. In measuring a reference within the focus detector 41, the position at which the AF light is directly received by the AF detection sensor 65 without reaching the wafer 3 serves as a reference for focus measurement by the focus detector 41. The focus position of the wafer 3 can be obtained from the difference between the reference in the focus detector 41 and the focus measurement result obtained for the wafer 3.

Focus measurement by the focus detector 41 shown in FIGS. 5 to 7 is performed not to measure a best focus position for detecting the mark 19 by the wafer alignment detector 16, but to detect the upper surface position of the wafer 3. Focus measurement by the focus detector 41 is an operation of setting the focus state of the image of the mark 19 in the wafer alignment detector 16 to fall within an allowable range. Since AF light reflected by the upper surface of the wafer 3 is detected, it is impossible to directly detect the focus position of a mark formed on the lower surface of the wafer 3.

The conventional method of obtaining a best focus position, at which the wafer alignment detector 16 detects the mark 19, when the mark 19 is positioned on the upper surface of the wafer 3 (conventional image autofocus measurement method) will be described with reference to FIGS. 8 and 9. In image autofocus measurement, first, the focus detector 41 projects AF light 42 onto the mark 19 on the upper surface of the wafer 3, and receives light reflected by it, as shown in FIG. 8. Although a configuration in which the focus detector 41 is positioned outside the wafer alignment detector 16 is shown in FIG. 8, that in which the focus detector 41 is positioned inside the wafer alignment detector 16 may be used. The focus position of the mark 19 on the upper surface of the wafer 3 can be obtained by driving the wafer stage 4 so that the position of the received reflected light coincides with the center of the AF detection sensor 65 of the focus detector 41. The focus position of the wafer alignment detector 16 can be almost matched with the mark 19 using the obtained focus position. FIG. 9 shows how the mark 19 is irradiated with measurement light 43 from the wafer alignment detector 16 while the wafer alignment detector 16 almost focuses on the upper surface of the wafer 3. Although the focus detector 41 focuses on the mark 19 on the upper surface of the wafer 3, it is necessary to obtain a focus position at which the contrast of the mark 19 having the image processed by the wafer alignment detector 16 maximizes. The wafer stage 4 is driven in the Z-direction from a state shown in FIG. 9, and alignment measurement is performed at each focus position by the wafer alignment detector 16, thereby detecting a focus position at which the contrast of the mark 19 maximizes (image autofocus measurement). In other words, the focus detector 41 measures the upper surface of the wafer 3 to allow the wafer alignment detector 16 to perform alignment measurement in the ±Z-directions with reference to the state in which the wafer alignment detector 16 almost focuses on the upper surface of the wafer 3.

Figure 10:
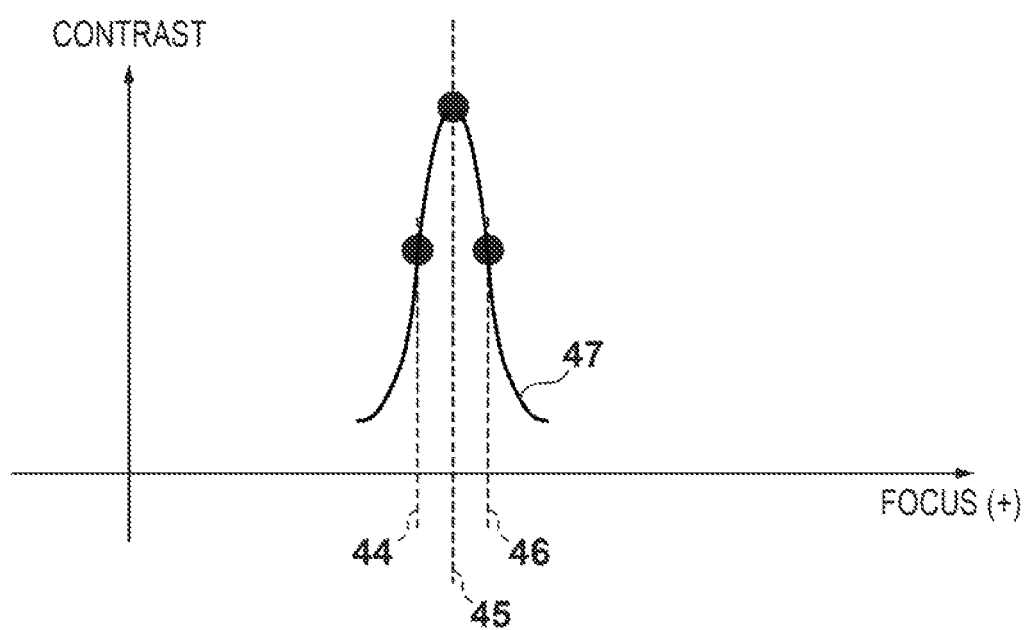
FIG. 10 is a graph showing a contrast curve obtained by image autofocus measurement.

From a state shown in FIG. 9, image autofocus measurement is performed by the wafer alignment detector 16 to obtain a contrast curve 47 shown in FIG. 10. A best focus position, having a maximum contrast, of the wafer alignment detector 16 can be obtained from data of the relationship between the focus position and the contrast. In obtaining a focus position having a maximum contrast, a method of obtaining the peak position of the contrast by quadratic fitting from a graph shown in FIG. 10 or centroid computation. Also, although three focus positions 44, 45, and 46 for image autofocus measurement are shown in FIG. 10 for the sake of simplicity, a larger number of measurement points such as 10 or 20 measurement points may be used. However, the larger the number of measurement points, the longer the measurement time becomes, leading to a decrease in throughput. Moreover, although the case wherein the mark 19 is formed on the upper surface of the wafer 3 has been described with reference to FIG. 8 as the conventional method of image autofocus measurement, the upper surface of the wafer 3 may be covered with a resist as long as the mark 19 is formed near the upper surface of the wafer 3.

Figure 11:
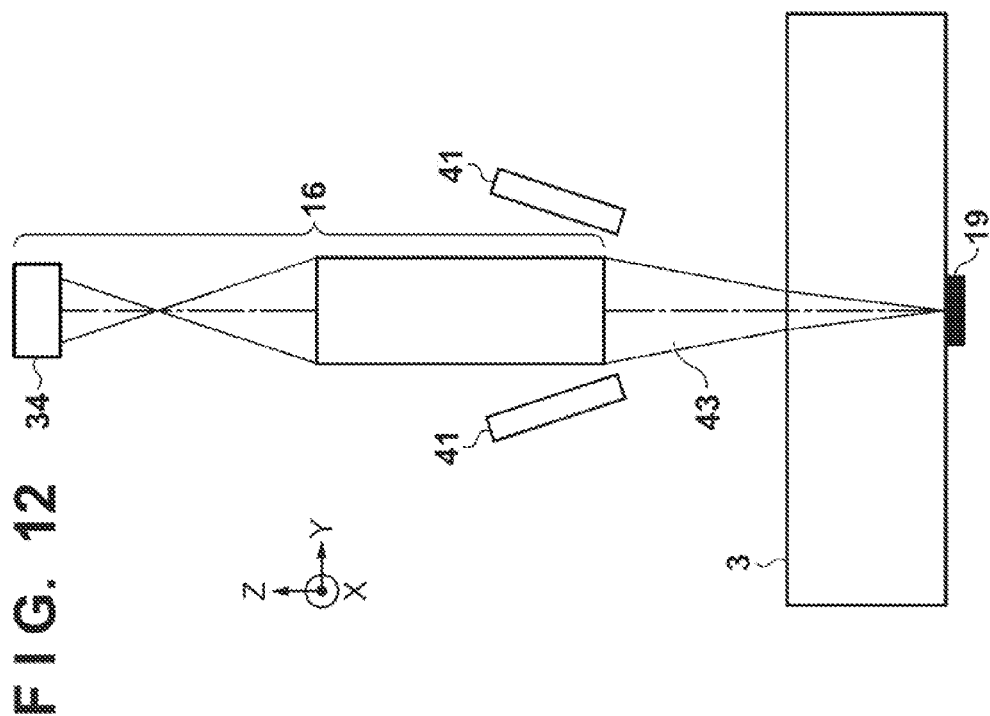
FIG. 11 is a view showing how the upper surface of a wafer having an alignment mark formed on its lower surface is measured by the AF detector.
Figure 12:
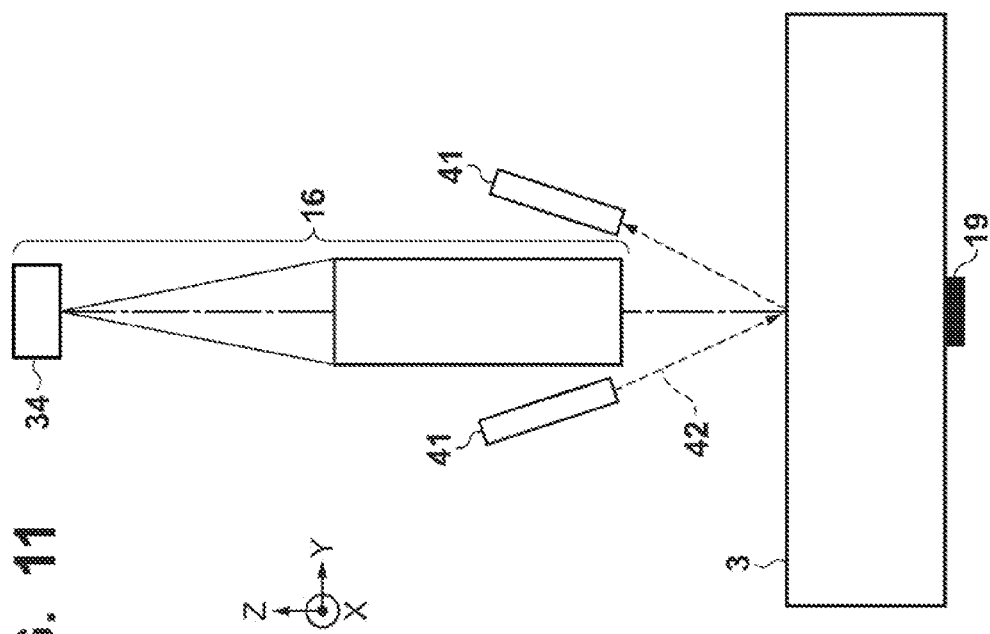
FIG. 12 is a view showing how the alignment mark formed on the lower surface is measured by the wafer alignment detector.

The case wherein the image autofocus measurement method is applied when the mark 19 is formed on the lower surface of the wafer 3 will be described below with reference to FIGS. 11 and 12. When the mark 19 is formed on the lower surface of the wafer 3 as well, first, the focus detector 41 projects the AF light 42 onto the upper surface of the wafer 3, and receives light reflected by it. At this time, the focus position of the upper surface of the wafer 3 can be obtained by driving the wafer stage 4 so that the position of the received reflected light coincides with the center of the AF detection sensor 65 of the focus detector 41. The focus position of the wafer alignment detector 16 can be almost matched with the upper surface of the wafer 3 using the obtained focus position. FIG. 12 shows how the upper surface of the wafer 3 is irradiated with the measurement light 43 from the wafer alignment detector 16 while the wafer alignment detector 16 almost focuses on the upper surface of the wafer 3. In a state shown in FIG. 12, the infrared light (measurement light) 43 incident on the mark 19 formed on the lower surface of the wafer 3 forms no image on the photoelectric conversion element 34 of the wafer alignment detector 16.

Figure 13:
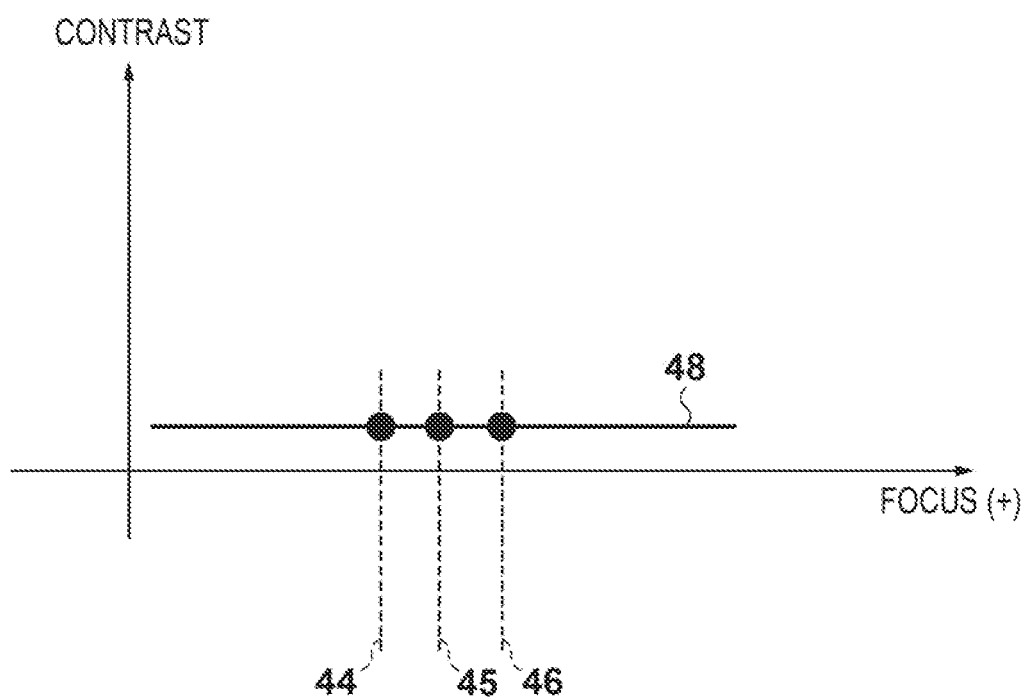
FIG. 13 is a graph showing the contrast curve of the conventional image autofocus on a wafer having an alignment mark formed on its lower surface.

When image autofocus measurement of the wafer alignment detector 16 is performed from a state shown in FIG. 12, a contrast curve 48 as shown in FIG. 13 is obtained. The contrast is low at each of the focus positions 44, 45, and 46, so the mark 19 on the lower surface of the wafer 3 cannot be detected. When the mark 19 is formed on the lower surface of the wafer 3, the wafer 3 often has a thickness of about several hundred micrometers, so the mark 19 on the lower surface of the wafer 3 cannot be quickly detected in image autofocus measurement which uses the upper surface of the wafer 3 detected by the focus detector 41 as a reference. When the range of image autofocus measurement which uses the upper surface of the wafer 3 as a reference considerably widens, the mark 19 on the lower surface of the wafer 3 can be detected by the wafer alignment detector 16 even if the wafer 3 has a thickness of several hundred micrometers. However, in this case, the number of measurement points considerably increases, so the measurement time prolongs, thus lowering the throughput.

Figure 14:
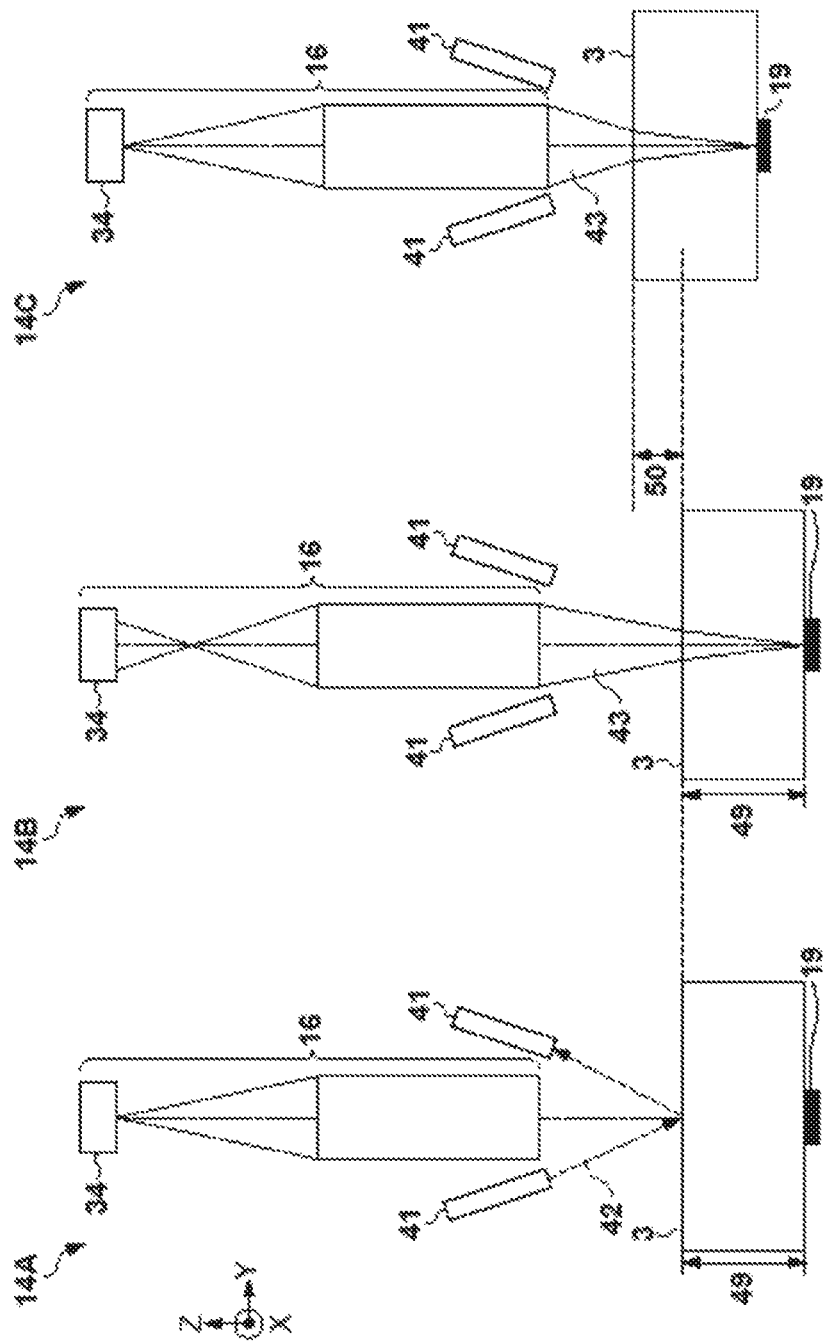
FIG. 14 is view showing how a wafer stage which corrects an offset due to the thickness of a wafer is driven.

A method of quickly obtaining a best focus position of the wafer alignment detector 16 even when the mark 19 is formed on the lower surface of the wafer 3 will be described below with reference to FIG. 14. In this method, to quickly obtain a best focus position of the mark 19 formed on the lower surface of the wafer 3, the start point of image autofocus measurement is determined using the thickness and refractive index of the wafer 3. Based on the thickness and refractive index of the wafer 3 input to an input device 18 shown in FIG. 3, a calculator 17 calculates the amount of offset for making the wafer alignment detector 16 focus on the mark 19 on the lower surface of the wafer 3, and instructs the wafer stage 4 to drive it by the obtained amount of offset. FIG. 14A shows how the upper surface of the wafer 3, having the mark 19 formed on its lower surface, is detected by the focus detector 41. When the state shown in FIG. 14A, in which the upper surface of the wafer 3 is detected by the focus detector 41, is maintained, the mark 19 cannot be detected by the wafer alignment detector 16 which almost focuses on the upper surface of the wafer 3, as shown in FIG. 14B. FIG. 14B shows how the measurement light 43 incident on the mark 19 formed on the lower surface of the wafer 3 forms an image on the photoelectric conversion element 34 of the wafer alignment detector 16. The wafer 3 has a thickness 49 of about several hundred micrometers, so the wafer alignment detector 16 is defocused by an amount (amount of offset 50) corresponding to this thickness in FIG. 14B.

An amount of offset 50 is calculated by the calculator 17 based on the thickness 49 of the wafer 3 and the refractive index of the wafer 3, which are input to the input device 18. From the state shown in FIG. 14A, in which the upper surface of the wafer 3 is measured by the focus detector 41, the wafer stage 4 is driven in the Z-direction by the amount of offset 50 calculated by the calculator 17. With this operation, the wafer alignment detector 16 can focus on the mark 19 on the lower surface of the wafer 3, as shown in FIG. 14C. The amount of offset 50 can be calculated in accordance with (Thickness 49 of Wafer 3)/(Refractive Index of Wafer 3). In, for example, an Si substrate having a thickness of 200 µm, 200 µm/3.5 (Refractive Index of Si)≈57 µm. In this manner, when the amount of offset 50 calculated from the thickness 49 and refractive index of the wafer 3 is used, image autofocus measurement can be quickly performed for the mark 19 on the lower surface of the wafer 3.

Figure 15:
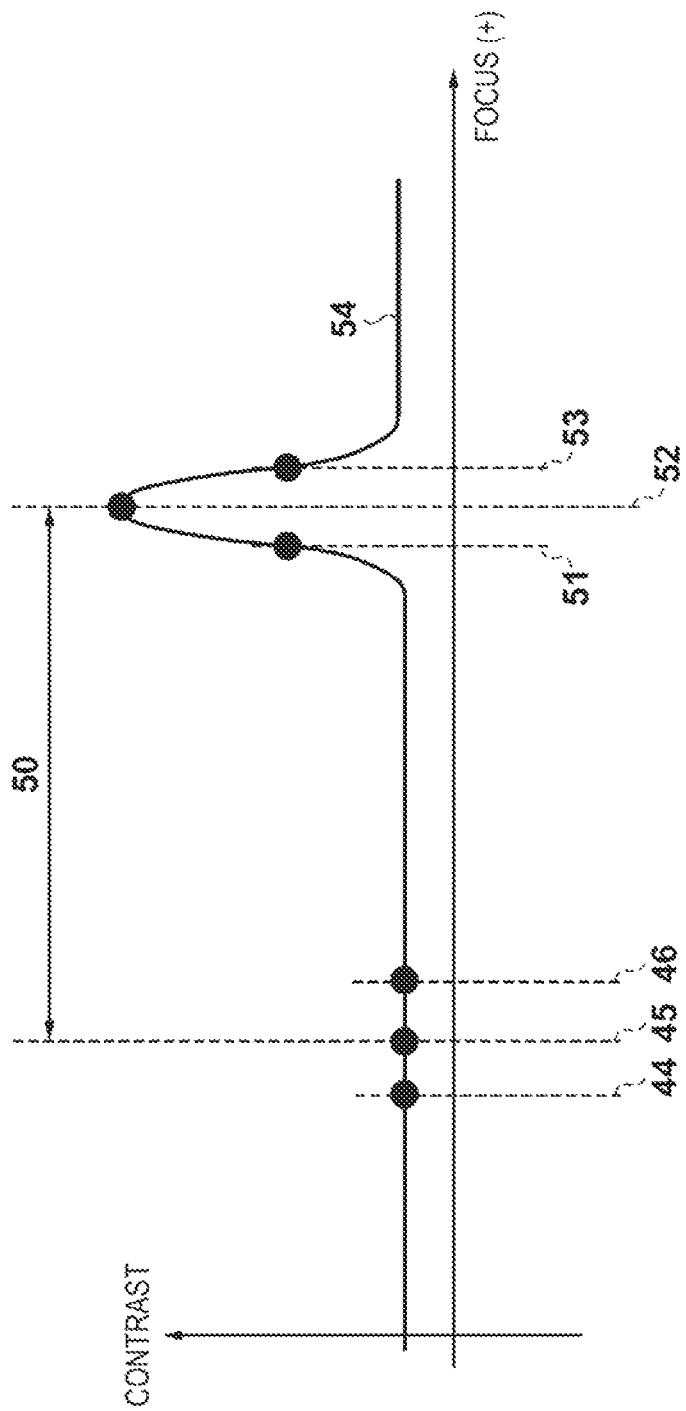
FIG. 15 is a graph showing the relationship between the contrast curve and the offset.

When image autofocus measurement is performed from a state shown in FIG. 14C, a contrast curve 54 of the right portion shown in FIG. 15 is obtained. The contrast is high at each of focus positions 51, 52, and 53 in FIG. 15, so the mark 19 on the lower surface of the wafer 3 can be detected by the wafer alignment detector 16. FIG. 13 shows a contrast curve when image autofocus measurement is performed from a state shown in FIG. 12 (and that shown in FIG. 14B), that is, from the upper surface of the wafer 3. Therefore, the contrast curve shown in FIG. 13 corresponds to that of the left portion shown in FIG. 15, including the focus positions 44 to 46. The difference between the focus positions 52 and 45 in the contrast curve 54 shown in FIG. 15 means the amount of offset 50. The wafer alignment detector 16 can quickly, accurately obtain the position of the mark 19 on the lower surface of the wafer 3 from data of the relationship between the focus position and the contrast as shown in FIG. 15.

In the foregoing description, the thickness and refractive index of the wafer 3 are input to the input device 18, and the amount of offset 50 can be calculated by the calculator 17 in accordance with (Thickness 49 of Wafer 3)/(Refractive Index of Wafer 3). However, the amount of offset 50 may be directly input to the input device 18. When the amount of offset 50 is directly input to the input device 18, it must be manually calculated in accordance with (Thickness 49 of Wafer 3)/(Refractive Index of Wafer 3), but the calculator 17 can be omitted, thus providing an advantage in terms of cost. The input device 18 and calculator 17 constitute a processor P which obtains the amount of offset 50, that is, information indicating a focus position to focus on the mark 19 in the wafer alignment detector 16. The information indicating a focus position can be information indicating a position to focus on the mark 19 in the wafer alignment detector 16 when the mark is detected by the wafer alignment detector 16 via the wafer 3, such as the amount of offset 50 and a position of the maximum value in the contrast curve 54.

Figure 16:
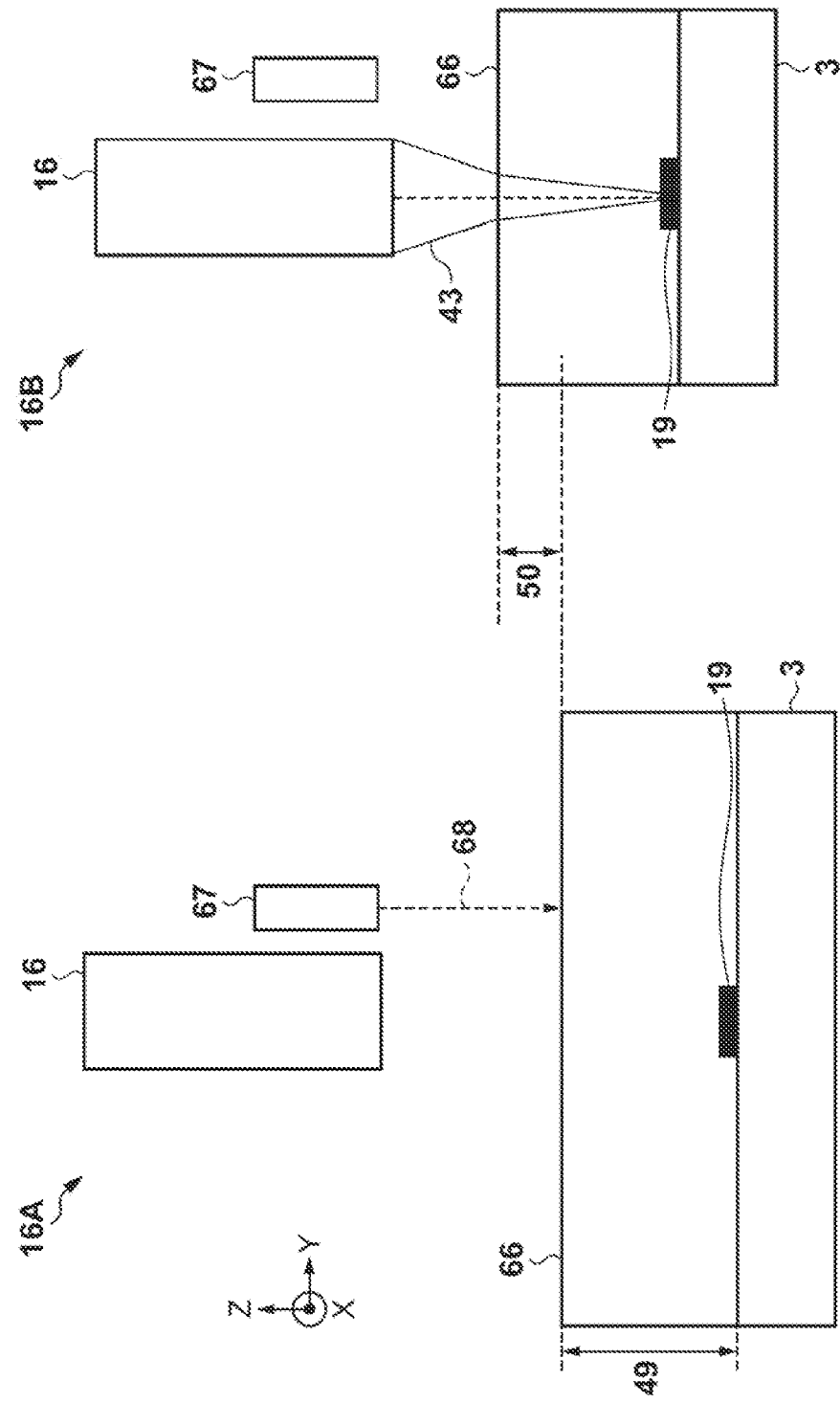
FIG. 16 is view showing how an alignment mark formed on the lower surface of a resist is measured.

In this embodiment, image autofocus measurement is performed for the mark 19, formed on the lower surface of the wafer 3, using the focus detector 41 which guides visible light to be obliquely incident on the wafer 3, and the wafer alignment detector 16 which uses infrared light. However, the position of the mark 19 formed on the lower surface of a resist 66 coated on the wafer 3 can be detected using the focus detector 41 and wafer alignment detector 16. FIG. 16 is view showing image autofocus measurement for the mark 19 formed on the lower surface of the resist 66. The above-mentioned focus detector 41 cannot detect the position of the upper surface of the resist 66 because visible light is transmitted through the resist 66, so an air focus detector 67 is used to detect the position of the upper surface of the resist 66. The air focus detector 67 is built into the wafer alignment detector 16, and therefore ejects air (gas) 68 toward the upper surface of the resist 66 to detect the level of the upper surface of the resist 66 based on the force (pressure) of air rebounded by the resist 66. Image autofocus measurement can be performed for the mark 19 on the lower surface of the resist 66 based on the level of the upper surface of the resist 66 detected by the air focus detector 67, and the thickness 49 and refractive index of the resist 66.

The wafer stage 4 is driven by the amount of offset 50 from a state shown in FIG. 16A, in which the upper surface position of the resist 66 is measured by the air focus detector 67. Then, the wafer alignment detector 16 can almost focus on the mark 19 on the lower surface of the resist 66, as shown in FIG. 16B. The amount of offset 50 can be calculated in accordance with (Thickness 49 of Resist 66)/(Refractive Index of Resist 66). In, for example, a resist 66 having a thickness of 200 µm, the amount of offset 50 becomes 200 µm/1.5 (Refractive Index of Resist 66)≈133 µm. When image autofocus measurement starts from a state shown in FIG. 16B, a best focus position of the mark 19 formed on the lower surface of the resist 66 can be quickly obtained. In this manner, when the amount of offset 50 calculated from the thickness and refractive index of a target object having the mark 19 on its lower surface is used, image autofocus measurement can be performed for the mark 19 formed on the lower surface of a target object other than the wafer 3.

As a sensor which measures the upper surface of the resist 66, a capacitance sensor, for example, may be adopted in place of the air focus detector 67. The capacitance sensor detects the amount of charges generated when a voltage is applied to the upper surface of the resist 66 to detect the height from the capacitance sensor to the upper surface of the resist 66. If the distance from the capacitance sensor to the upper surface of the resist 66 is small, the amount of charges generated when a voltage is applied to this surface is large. However, if the distance from the capacitance sensor to the upper surface of the resist 66 is large, the amount of charges generated when a voltage is applied to this surface is small. In this manner, the amount of charges generated when a predetermined voltage is applied across the capacitance sensor and the upper surface of the resist 66 is detected, thereby calculating the distance from the capacitance sensor to the upper surface of the resist 66.

When the exposure apparatus exposes 25 wafers 3 in one lot to light, image autofocus measurement is performed for the mark (first mark) 19 on the first wafer 3. The marks (second marks) 19 on the second and subsequent wafers 3 can be focused based only on the measurement result obtained by the focus detector 41. Image autofocus measurement is performed for the mark 19 formed on the lower surface of the first wafer 3 in one lot while the wafer stage 4 is driven by the amount of offset 50 from the measurement value obtained by the focus detector 41, as shown in FIG. 14C. At this time, a difference 69 between a best focus position of the wafer alignment detector 16 relative to the mark 19 on the lower surface of the wafer 3, which is calculated by image autofocus measurement, and the focus position obtained by measuring the upper surface of the wafer 3 by the focus detector 41 is calculated. As for the second and subsequent wafers 3, the wafer stage 4 is driven by the difference 69 obtained from image autofocus measurement of the first wafer 3 from the state in which the upper surface position of the wafer 3 is measured by the focus detector 41. In this state, the mark 19 formed on the lower surface of the wafer 3 is measured by the wafer alignment detector 16. In this manner, by performing image autofocus measurement only for the first wafer 3, alignment measurement can be performed for the remaining 24 wafers 3 with high accuracy.

Second Embodiment

In the first embodiment, the focus position of the wafer alignment detector 16 relative to the mark 19 formed on the lower surface of the wafer 3 is quickly obtained using the focus detectors 41 and 67 which detect the upper surface position of the wafer 3. In the second embodiment, a wafer alignment detector which can switch between two detection modes: first and second detection modes is used as a wafer alignment detector 16. Also, in the second embodiment, the focus detectors 41 and 67 which detect the upper surface position of the wafer 3, that are used in the first embodiment, are not used. The wafer alignment detector 16 detects a mark 19 with a first detection accuracy while changing the interval between marks 19 at a first pitch in the first detection mode, and detects the mark 19 with a second detection accuracy while changing the interval between the marks 19 at a second pitch in the second detection mode. In this case, the second pitch is smaller than the first pitch, and the second detection accuracy is higher than the first detection accuracy. That is, in the first detection mode, a wide pitch at which the detection accuracy is low but a wide region can be detected at once is set. On the other hand, in the second detection mode, a fine pitch at which the detection region is narrow but the detection accuracy is high is set.

Figure 17:
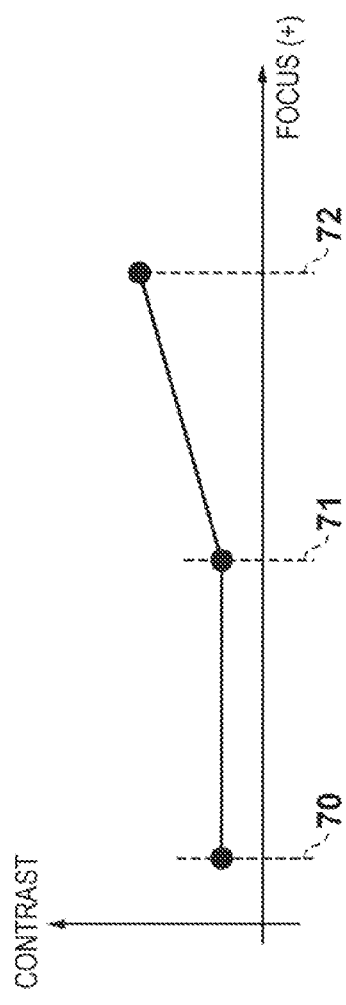
FIG. 17 is a graph showing a contrast curve at a wide pitch.
Figure 18:
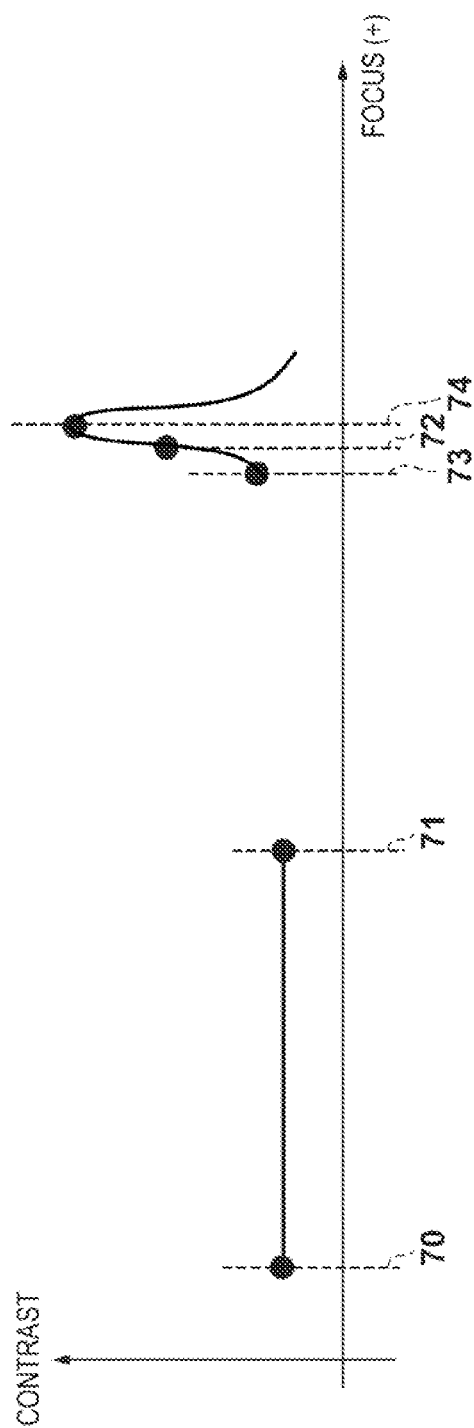
FIG. 18 is a graph showing a contrast curve at a fine pitch.

FIG. 17 is a graph showing a contrast curve when the mark 19 formed on the lower surface of a wafer 3 is measured in the first detection mode in which a wide pitch is set for the wafer alignment detector 16 positioned on the upper surface of the wafer 3. A rough focus position 72 for measuring the mark 19 can be quickly obtained by performing image autofocus measurement in the first detection mode in which a pitch wider than that of the conventional image autofocus measurement of the wafer alignment detector 16 is set. The detection mode of the wafer alignment detector 16 is switched to the second detection mode in which the detection accuracy is high, and image autofocus measurement starts from the focus position 72. In this manner, a best focus position for measuring the mark 19 can be quickly obtained by switching the detection mode of the wafer alignment detector 16 to perform two-step image autofocus measurement. FIG. 18 shows a contrast curve when image autofocus measurement is performed in the second detection mode from the focus position 72 obtained in the first detection mode, and reveals that a best focus position 74 can be obtained.

Reference Example

In the first embodiment, both the wafer alignment detector 16 and focus detector 41 for detecting the mark 19 on the lower surface of the wafer 3 are positioned on the upper surface of the wafer 3. However, if it is possible to position the wafer alignment detector 16 or the focus detector 41 on the lower surface of the wafer 3, the wafer alignment detector 16 and focus detector 41 can also be positioned separately on the upper and lower surfaces of the wafer 3. FIG. 19 is view illustrating an example of the layout of a wafer alignment detector 16 and a focus detector 41. FIG. 19A illustrates an example of the layout according to the first embodiment, in which both a wafer alignment detector 16 and a focus detector 41 are positioned on the upper surface of the wafer 3. FIG. 19B illustrates an example of the layout in which to detect the mark 19 on the lower surface of the wafer 3, a wafer alignment detector 16 which uses infrared light as a light source is positioned on the upper surface of the wafer 3, while a focus detector 41 which uses visible light as a light source is positioned on the lower surface of the wafer 3. FIG. 19C illustrates an example of the layout in which to detect the mark 19 on the lower surface of the wafer 3, a wafer alignment detector 16 which uses visible light as a light source is positioned on the lower surface of the wafer 3, while an focus detector 41 which uses infrared light as a light source is positioned on the upper surface of the wafer 3.

[Method of Manufacturing Device]

A method of manufacturing a device (for example, a semiconductor device or a liquid crystal display device) will be described next. A semiconductor device is manufactured by a preprocess of forming an integrated circuit on a wafer, and a post-process of completing, as a product, a chip of the integrated circuit formed on the wafer by the preprocess. The preprocess includes a step of exposing a wafer coated with a photosensitive agent to light using the above-mentioned exposure apparatus, and a step of developing the wafer. The post-process includes an assembly step (dicing and bonding) and packaging step (encapsulation). A liquid crystal display device is manufactured by a step of forming a transparent electrode. The step of forming a transparent electrode includes a step of coating with a photosensitive agent a glass substrate on which a transparent conductive film is deposited, a step of exposing the glass substrate coated with the photosensitive agent to light using the above-mentioned exposure apparatus, and a step of developing the glass substrate. The method of manufacturing a device according to this embodiment can manufacture a device with a quality higher than those of a device manufactured by the conventional technique.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-048611, filed Mar. 5, 2012, which is hereby incorporated by reference herein in its entirety.

What is claimed is:

1. A detection apparatus which detects a mark formed on a substrate permeable to infrared light and impermeable to visible light, the apparatus comprising:
   a first detector configured to detect a first mark formed on an upper surface of the substrate and a second mark formed on a lower surface of the substrate;
   a second detector configured to detect an upper surface position of the substrate for a focusing of the first detector; and
   a processor configured to perform detection processing of the first and second marks using the first and second detectors,
   wherein the first detector comprises:
      a light source configured to emit selectively visible light and infrared light;
      a photoelectric conversion device; and
      an optical system configured to form an image of the first mark on a light-receiving surface of the photoelectric conversion device using the visible light emitted by the light source, applied to the first mark from an upper surface side of the substrate, and reflected by the first mark, and to form an image of the second mark on the light-receiving surface of the photoelectric conversion device using the infrared light emitted by the light source, applied to the second mark from the upper surface side of the substrate, and reflected by the second mark;
   wherein in a case of detecting the first mark, the processor performs:
      a detection of the upper surface position of the substrate using the second detector; and
      a focusing of the first detector using the visible light while adjusting a distance of the substrate with respect to the first detector within a range including the detected upper surface position,
   and wherein in a case of detecting the second mark, the processor performs:
      a detection of the upper surface position of the substrate using the second detector; and
      a focusing of the first detector using the infrared light while adjusting a distance of the substrate with respect to the first detector within a range including a position offset by an offset amount based on a thickness of the substrate.

2. The apparatus according to claim 1, wherein the processor obtains the offset amount based on the thickness of the substrate and a refractive index of the substrate.

3. The apparatus according to claim 1, wherein the second detector guides light to be obliquely incident on the upper surface of the substrate, and detects the light reflected by the upper surface of the substrate to detect the upper surface position of the substrate.

4. The apparatus according to claim 1, wherein said second detector is configured to eject a gas toward an upper surface of the substrate and detect a pressure of the gas rebounded by the upper surface of the substrate to detect the upper surface position of the substrate.

5. The apparatus according to claim 1, wherein said second detector is configured to detect an amount of charge generated when a voltage is applied onto an upper surface of the substrate to detect the upper surface position of the substrate.

6. An exposure apparatus which exposes a substrate to light, the apparatus comprising:
   a detection apparatus configured to detect a mark formed on a substrate as a target object, or a mark arranged on a resist as a target object coated on the substrate, wherein the substrate is permeable to infrared light and impermeable to visible light;
   a substrate stage which holds the substrate; and
   a control unit which controls the substrate stage to set a focus state of the mark to fall within an allowable range,
   the detection apparatus including:
   a first detector which detects a first mark formed on an upper surface of the substrate and a second mark formed on a lower surface of the substrate;
   a second detector configured to detect an upper surface position of the substrate for a focusing of the first detector; and
   a processor configured to perform detection of the first and second marks using the first and second detectors,
   wherein the first detector comprises:
      a light source configured to emit selectively visible light and infrared light;
      a photoelectric conversion device; and
      an optical system configured to form an image of the first mark on a light-receiving surface of the photoelectric conversion device using the visible light emitted by the light source, applied to the first mark from an upper surface side of the substrate, and reflected by the first mark, and to form an image of the second mark on the light-receiving surface of the photoelectric conversion device using the infrared light emitted by the light source, applied to the second mark from the upper surface side of the substrate, and reflected by the second mark;

wherein in a case of detecting the first mark, the processor performs:
   a detection of the upper surface position of the substrate using the second detector; and
   a focusing of the first detector using the visible light while adjusting a distance of the substrate with respect to the first detector within a range including the detected upper surface position,
and wherein in a case of detecting the second mark, the processor performs:
   a detection of the upper surface position of the substrate using the second detector; and
   a focusing of the first detector using the infrared light while adjusting a distance of the substrate with respect to the first detector within a range including a position offset by an offset amount based on a thickness of the substrate,
wherein the control unit controls the substrate stage based on the focusing of the first detector by the processor.

7. The apparatus according to claim 6, wherein the processor
   obtains information of an offset amount from an upper surface position of a first substrate in a lot detected by the second detector for focusing on an image of a first mark, formed on a lower surface of the first substrate in the lot, in the first detector, and
   obtains information indicating focus position for focusing on an image of a second mark, formed on a lower surface of a second substrate or subsequent substrate in the lot, in the first detector, based on the information of the offset amount from the upper surface position of the first substrate and upper surface position of the second substrate or the subsequent substrate detected by the second detector.

8. A method of manufacturing a device, the method comprising:
   exposing a substrate to light using an exposure apparatus;
   developing the exposed substrate; and
   processing the developed substrate to manufacture the device,
   the exposure apparatus including:
   a detection apparatus configured to detect a mark formed on the substrate as a target object, or a mark arranged on a resist as a target object coated on the substrate, wherein the substrate is permeable to infrared light and impermeable to visible light;
   a substrate stage which holds the substrate; and
   a control unit which controls the substrate stage to set a focus state of the mark to fall within an allowable range,
   the detection apparatus including:
   a first detector configured to detect a first mark formed on an upper surface of the substrate and a second mark formed on a lower surface of the substrate;
   a second detector configured to detect an upper surface position of the substrate for a focusing of the first detector; and
   a processor configured to perform detection of the first and second marks using the first and second detectors,
   wherein the first detector comprises:
      a light source which selectively emits visible light and infrared light;
      a photoelectric conversion device; and
      an optical system which forms an image of the first mark on a light-receiving surface of the photoelectric conversion device using the visible light emitted by the light source, applied to the first mark from an upper surface side of the substrate, and reflected by the first mark, and to form an image of the second mark on the light-receiving surface of the photoelectric conversion device using the infrared light emitted by the light source, applied to the second mark from the upper surface side of the substrate, and reflected by the second mark;
   wherein in a case of detecting the first mark, the processor performs:
      a detection of the upper surface position of the substrate using the second detector; and
      a focusing of the first detector using the visible light while adjusting a distance of the substrate with respect to the first detector within a range including the detected upper surface position,
   and wherein in a case of detecting the second mark, the processor performs:
      a detection of the upper surface position of the substrate using the second detector; and
      a focusing of the first detector using the infrared light while adjusting a distance of the substrate with respect to the first detector within a range including a position offset by an offset amount based on a thickness of the substrate,
   wherein the control unit controls the substrate stage based on the focusing of the first detector by the processor.

* * * * *